(12) United States Patent
Dencovski et al.

(10) Patent No.: US 11,712,210 B2
(45) Date of Patent: Aug. 1, 2023

(54) MOBILE PLATFORM

(71) Applicant: Siemens Healthcare GmbH, Erlangen (DE)

(72) Inventors: Kristian Dencovski, Erlangen (DE); Elmar Garcia, Erlangen (DE); Joerg Hofmann, Forchheim (DE); Oliver Patrick Welzel, Graefenberg (DE); Chihebeddine Dahmani, Erlangen (DE); Franz Dirauf, Bad Staffelstein (DE)

(73) Assignee: Siemens Healthcare GMBH, Erlangen (DE)

( * ) Notice: Subject to any disclaimer, the term of this patent is extended or adjusted under 35 U.S.C. 154(b) by 274 days.

(21) Appl. No.: 17/144,395

(22) Filed: Jan. 8, 2021

(65) Prior Publication Data

US 2021/0219927 A1   Jul. 22, 2021

(30) Foreign Application Priority Data

Jan. 16, 2020   (EP) ..................................... 20152164

(51) Int. Cl.
*A61B 6/00* (2006.01)
*A61B 6/10* (2006.01)
*A61B 90/35* (2016.01)
*A61B 1/00* (2006.01)
*A61B 6/04* (2006.01)
*A61B 8/00* (2006.01)

(52) U.S. Cl.
CPC .......... *A61B 6/102* (2013.01); *A61B 1/00149* (2013.01); *A61B 6/0407* (2013.01); *A61B 6/4458* (2013.01); *A61B 6/504* (2013.01); *A61B 6/547* (2013.01); *A61B 8/40* (2013.01); *A61B 8/4218* (2013.01); *A61B 8/4254* (2013.01); *A61B 8/4263* (2013.01); *A61B 90/35* (2016.02)

(58) Field of Classification Search
CPC ... A61B 1/00149; A61B 6/0407; A61B 6/102; A61B 6/4405; A61B 6/4441; A61B 6/4458; A61B 6/504; A61B 6/547
See application file for complete search history.

(56) References Cited

U.S. PATENT DOCUMENTS

| | | |
|---|---|---|
| 2010/0299014 A1 | 11/2010 | Bouvier |
| 2015/0216746 A1 | 8/2015 | Dirauf et al. |
| 2015/0320367 A1 | 11/2015 | Dirauf et al. |
| 2017/0325763 A1 | 11/2017 | Hoernig et al. |
| 2018/0031377 A1 | 2/2018 | Guo et al. |
| 2018/0177523 A1 | 6/2018 | Piron et al. |
| 2019/0209104 A1 | 7/2019 | Dirauf et al. |
| 2019/0343701 A1 | 11/2019 | Dirauf et al. |

FOREIGN PATENT DOCUMENTS

| | | |
|---|---|---|
| CN | 109288541 A | 2/2019 |
| DE | 102014202033 A1 | 8/2015 |
| DE | 102014208540 A1 | 11/2015 |

(Continued)

*Primary Examiner* — Dani Fox
(74) *Attorney, Agent, or Firm* — Harness, Dickey & Pierce, P.L.C.

(57) ABSTRACT

A mobile platform includes a chassis, a sensor module and at least one holding mechanism. In an embodiment, the at least one holding mechanism is designed to guide a first medical device and is configured to position the first medical device in at least one operating position within an adjusting range.

18 Claims, 5 Drawing Sheets

(56) References Cited

FOREIGN PATENT DOCUMENTS

| | | | |
|---|---|---|---|
| DE | 102016208123 A1 | 9/2017 | |
| DE | 202020105282 U1 | 10/2020 | |
| EP | 2380496 A1 * | 10/2011 | ........... A61B 6/0457 |
| EP | 2380496 A1 | 10/2011 | |
| EP | 3454754 A1 | 3/2019 | |
| EP | 3534860 A1 | 9/2019 | |
| WO | WO 2019228530 A1 | 12/2019 | |

* cited by examiner

MOBILE PLATFORM

PRIORITY STATEMENT

The present application hereby claims priority under 35 U.S.C. § 119 to European patent application number EP20152164.8 filed Jan. 16, 2020, the entire contents of which are hereby incorporated herein by reference.

FIELD

Example embodiments of the application generally relate to a mobile platform and to a system comprising a plurality of inventive mobile platforms.

BACKGROUND

Medical devices for diagnosis and treatment are, as a rule, arranged to be stationary and often require a lot of effort to install and a specific building infrastructure. In addition, it is often necessary for a patient to assume a particular position in order to be examined or treated with the medical device. For example, for an X-ray record of the thorax, the patient has to position themselves with their chest directly in front of an X-ray detector or detector attached to a stand. In some cases the position of the detector can be adjusted to the height of patient. If the patient is in a wheelchair, however, appropriate positioning of the patient is more difficult.

In addition, the transportation of medical devices and material within a hospital or a doctor's surgery causes additional work for the medical staff. For this reason, mobile medical devices are increasingly being used in addition to stationary devices in the medical field. These mobile medical devices are typically designed to be mobile and/or portable. Such mobile medical devices can, if required, be used at different locations, and when they are not being used can be temporarily removed from their work environment and be parked at a suitable location.

For example, mobile patient couches or patient beds are used for transporting patients in the hospital. In particular, the patient couches of medical imaging devices can be designed to be mobile themselves, so the workflow can be simplified. Furthermore, medical imaging devices can be designed to be mobile, wherein in particular their gantry can be designed to be mobile. In particular, mobile X-ray systems, mobile diagnostic stations, mobile devices for intensive care and mobile robotic systems are known for medical applications. Conventional mobile medical devices usually provide only limited functionality, however, and operate less efficiently than stationary devices.

For medical imaging, in particular for radiological and nuclear medical imaging, the use of holding and/or guiding systems, such as floor-, ceiling- or wall-mounted rail systems and/or holding structures and robot arms, etc. is known (for example radiography systems, angiography systems, etc.). Alternatively, imaging systems with rigid geometric arrangement of the system mechanics (for example mobile X-ray systems, X-ray-computed tomography units, magnetic resonance tomography systems etc.) are used. The holding and/or guiding systems are designed for positioning the medical devices.

Positioning of the medical devices is limited or restricted by the holding and/or guiding system in this case. Imaging systems with a rigid geometric arrangement cannot be freely positioned or cannot be positioned in accordance with the needs of the patient. Medical devices can be, for example, X-ray tubes, X-ray detectors, ultrasound heads, endoscopes, etc.

Robotic systems or robot-assisted platforms can currently be used in medical interventions, in particular in cardiovascular and peripheral vascular intervention. These are used for movement, manipulation or for positioning guide catheters, guide wires, balloon implants or stent implants with the aid of integrated imaging, preferably camera imaging. The doctor controls the procedure via a remote control module and is protected from X-ray radiation, therefore. The robotic system is typically permanently connected to the patient table and consequently cannot be used with other imaging systems such as further angiography systems of a medical facility.

In addition, owing to the fixed arrangement of the robotic system, the angulation range of an angiography system is typically significantly limited. Access to the patient in the event of complications or emergencies can also be impeded by the fixed position of the robotic system, and this can lead to a direct risk to the patient.

Mobile medical devices are currently transported manually to the point of use and, as a rule, also manually positioned and adjusted for the respective application. For image-assisted treatment, different systems (imaging plus actuating elements and optionally further devices) have until now been manually registered in a laborious and time-consuming manner.

SUMMARY

Embodiments of the invention may provide devices which enable spatially flexible and automatic positioning of medical devices; and/or may enable automatic static and dynamic imaging and provide autonomous assistance functions.

Embodiments of the invention include a mobile platform, and/or a system comprising a plurality of mobile platforms. Preferred and/or alternative, advantageous variants are the subject manner of the claims.

In an embodiment, the invention relates to a mobile platform, which comprises a chassis, a sensor module and at least one holding mechanism. The at least one holding mechanism is designed for guiding a first medical device and is configured in such a way as to position the first medical device in at least one operating position within an adjusting range.

According to a further embodiment, the invention relates to a system, which comprises a plurality of inventive mobile platforms of at least one embodiment. The plurality of inventive mobile platforms is coordinated among themselves. In particular, one mobile platform from the plurality of mobile platforms can be moved relative to the position or movement of a different mobile platform from the plurality of mobile platforms.

According to an embodiment, the invention relates to a mobile platform, comprising:

a chassis;

a sensor module; and at least one holding mechanism designed to guide a first medical device, the at least one holding mechanism being configured to position the first medical device in at least one operating position within an adjusting range.

According to an embodiment, the invention relates to a system, comprising:

a plurality of mobile platforms, each of the plurality of mobile platforms including,
a chassis,
a sensor module, and
at least one holding mechanism designed to guide a first medical device, the at least one holding mechanism being configured to position the first medical device in at least one operating position within an adjusting range, wherein each of the plurality of mobile platforms are coordinated among other of the plurality of mobile platforms.

BRIEF DESCRIPTION OF THE DRAWINGS

The above-described properties, features and advantages of this invention will become clearer and more comprehensible in conjunction with the following figures and their descriptions. The figures and descriptions are not intended to restrict the invention and its embodiments in any way. Identical components are provided with corresponding reference numerals in the different figures. As a rule, the figures are not to scale.

In the drawings.

DETAILED DESCRIPTION OF THE EXAMPLE EMBODIMENTS

Figure 1:
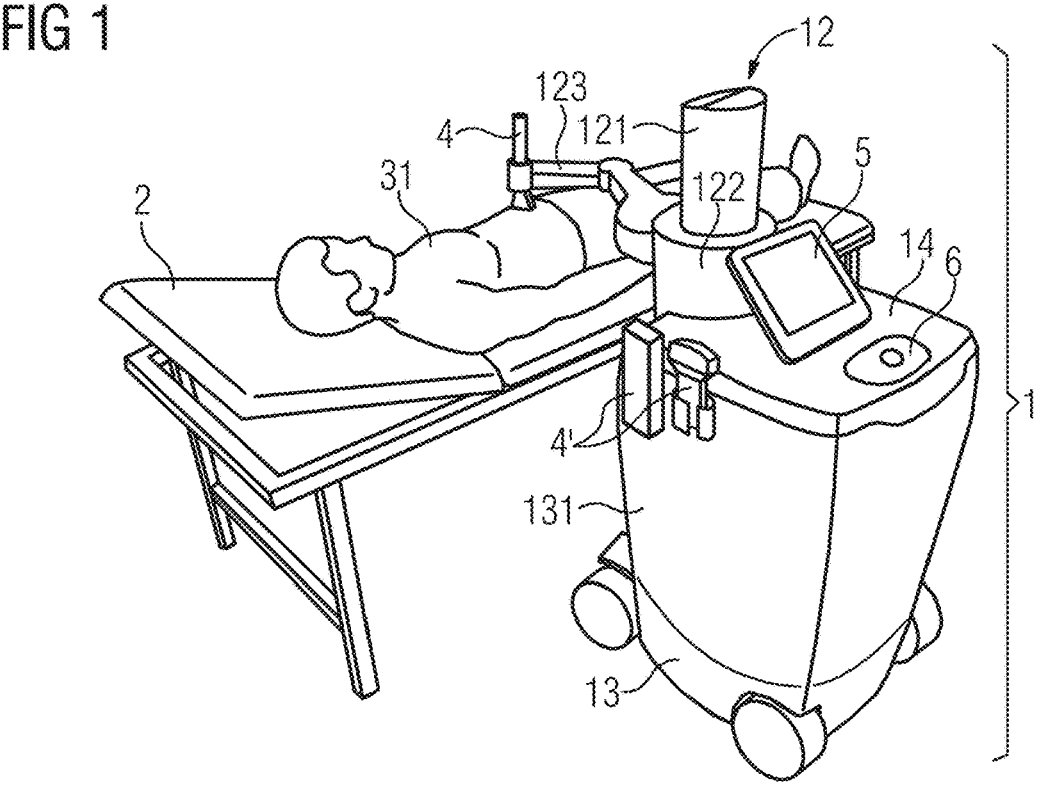
FIG. 1 shows a view of an example embodiment of an inventive mobile platform for the automatic performance of ultrasound examinations.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a first embodiment, the invention relates to a mobile platform, which comprises a chassis, a sensor module and at least one holding mechanism. The at least one holding mechanism is designed for guiding a first medical device and is configured in such a way as to position the first medical device in at least one operating position within an adjusting range.

The chassis is used to displace or move the mobile platform comprising all elements or components. In particular, the mobile platform can assume various positions via the chassis. The chassis advantageously comprises a drive unit and a transport unit. The transport unit can comprise at least one roller or at least one wheel or at least one cylinder or at least one chain for moving the chassis.

The drive unit drives the transport unit. The drive unit is advantageously designed as a motor, preferably as an electric motor. In particular, the electric motor is designed as an electromechanical converter. In other words, the electric motor converts electrical energy into mechanical energy. Alternatively, the motor can also be designed to convert thermal, chemical, hydraulic or pneumatic energy into mechanic energy. In particular, the mechanical energy can be used to drive the transport unit.

The sensor module comprises at least one, preferably a large number of, sensor(s), which are used to detect the environment of the mobile platform. The at least one sensor is advantageously designed to detect at least one, preferably a plurality of, environmental parameter(s). The environmental parameter can comprise, in particular, a position of the mobile platform or a distance of the mobile platform from other objects, people, etc. or a position of a patient. In particular, the environmental parameter(s) can comprise the movement or position of other devices, people, etc.

The at least one holding mechanism is designed in such a way that it holds the first medical device and can move or position it in a desired operating position. In particular, the at least one holding mechanism can position the first medical device within an adjusting range. The adjusting range can comprise a range of 0 cm to 300 cm in height. This range advantageously comprises a range between 50 cm and 250 cm. In embodiments, the adjusting range includes the height of any patient. In embodiments, the adjusting range is dependent on the choice of the first medical device. The first medical device is advantageously designed for performing a medical examination or for a medical procedure or for assistance in a medical procedure. The adjusting range is limited by the design of the at least one holding mechanism. In example embodiments, the adjusting range, depending on the design of the holding mechanism, can comprise a three-dimensional range in which the first medical device can be positioned via the at least one holding mechanism.

In embodiments, positioning of the first medical device in at least one operating position can comprise rotating, tilting or a height adjustment of the first medical device with the aim of positioning the first medical device in the at least one operating position. The at least one operating position is defined by a task of the first medical device. The first medical device can perform its task in the at least one operating position. The task of the medical device is, for example, to perform a medical examination or a medical procedure or an assistance function. The medical examination can be an imaging examination of a patient, for example an X-ray, an ultrasound, a sectional image, etc. or a combination of such imaging methods. The medical procedure can be, for example, an endoscopy, a surgical procedure, a minimally invasive procedure, etc. The assistance function can be transporting materials for a medical examination, etc.

In particular, the at least one holding mechanism can be designed in such a way that it moves or guides the first medical device on a specified trajectory. In embodiments, the trajectory can be specified by an operator. Alternatively, the trajectory can be defined as a standard trajectory for a particular examination, for example for a tomography of the abdomen of a patient. Alternatively, the trajectory can be instantaneously calculated from the various environmental parameters, which are detected with the sensor module.

In embodiments, the holding mechanism can be designed to be moved automatically to move or guide the first medical device, for example along a specified trajectory. In embodiments, the holding mechanism can also be designed to be moved manually by a user and in particular via remote control. In other words, the holding mechanism can be designed to transfer a control command of a remote user, received substantially simultaneously via a remote operating interface, via a control unit into a movement of the holding mechanism for positioning the first medical device.

Guiding describes moving of the first medical device via the at least one holding mechanism. Moving can be used for positioning the first medical device in the at least one operating position. Alternatively, moving can be used for following a trajectory, which comprises a plurality of operating positions.

In embodiments, the first medical device is from the following group of medical devices: X-ray detector, X-ray tube, ultrasound head, endoscope, interventional platform, work light, medical instrument or medical material.

In a preferred variant, the X-ray detector or detector is a flat panel detector or X-ray flat panel detector. It can be a semiconductor or a scintillation detector. In a preferred embodiment, the X-ray detector is a digital X-ray detector.

The X-ray tube is advantageously a rotating anode X-ray tube. Alternatively, the X-ray tube can also be a transmission anode X-ray tube. The X-ray tube comprises an exit port from which the X-ray radiation advantageously exits as a cone beam.

The ultrasound head can advantageously be designed as a sector scanner, linear scanner or convex scanner. The ultrasound head is designed for sending and receiving ultrasound waves with a piezo crystal.

The endoscope or the interventional platform is in each case designed for performing minimally invasive procedures or minimally invasive examinations. The endoscope can be rigid or flexible in design. The endoscope or the interventional platform can in each case be designed to introduce different medical instruments, such as catheters, guide catheters, guide wires, ablation instruments, graspers, cameras, etc. into a patient. The endoscope or the interventional platform can in each case comprise a camera, which optically encompasses the interventional environment of the endoscope and/or the interventional platform. The endoscope or the interventional platform can also be designed to introduce medical implants such as ball or stent implants into a patient. The endoscope or the interventional platform can comprise one or more medical instrument(s) and/or one or more medical implant(s) at least temporarily for this purpose. In embodiments, the endoscope or the interventional platform can be designed to move a medical instrument and/or a medical implant, to displace it, to place it at a desired position, to deform it or the like.

In embodiments, the interventional platform can comprise an endoscope.

The work light is designed for illuminating a medical operating area or examination area. The work light comprises a lamp, which emits visible light. The light can advantageously be diffuse or be emitted so it is directed onto a small area.

In particular, the medical instrument can be a syringe, a catheter, an ablation instrument, surgical instruments, a camera, etc. In particular, the medical instrument can be all further instruments, which are used in a hospital or in a doctor's surgery and have to be moved. In particular, the medical material can be a container with ultrasound gel, gauze or swabs. In particular, the medical material can be all further consumable items, which are used in a hospital or doctor's surgery.

In embodiments, the first medical device can be any device, which is necessary for a diagnosis or the medical examination or the medical procedure or for assistance in the medical procedure on a patient.

In embodiments, the medical device is designed so it can be controlled, monitored or moved via appropriate operating interface or control module manually or automatically, directly or remotely via a control unit provided for this purpose. For example, a medical device in the form of endoscope can be controlled manually. An interventional platform can preferably be controlled remotely.

In embodiments, the at least one holding mechanism comprises a lifting device, a rotating device, a robotic actuator and/or a manipulation device.

In particular, the mobile platform can comprise a housing, to or on which the holding mechanism can be attached or arranged. The terms attached to the housing and attached to the chassis will be used synonymously below. The first medical device can be attached to or arranged on the lifting device or rotating device or robotic actuator or manipulation device. In particular, the first medical device can be guided by the lifting device or rotating device or robotic actuator or manipulation device. The elements or components of the at least one holding mechanism can be combined in any way. For a combination the elements are coupled together, in other words, the elements are attached to each other. In particular, for example, at least one of these attachments can be detachable. In particular, a detachable attachment can be formed by at least one screw or a clip or a groove or a snap-fit, etc. The terms attached and coupled will be used synonymously. Elements or components of the holding mechanism can be the lifting device, rotating device, robotic actuator and/or manipulation device.

The lifting device is configured for carrying out linear adjusting movements. It is preferably used for adjusting the height of the first medical device in the vertical direction. The lifting device covers the operating positions of the first medical device in terms of height. Advantageously, the lifting device encompasses a height of 0 cm to 300 cm. The encompassed height can depend on the first medical device or on the task of the first medical device but can also be universally provided for any medical device, so the mobile platform can be used particularly flexibly. In embodiments, the lifting device can have a telescopic design and, for the adjustment of smaller heights, telescopic sections that are ever narrower in height and can be moved inside one another. In alternative embodiments, the lifting device corresponds to a rail, which is used for height adjustment. The first medical device can be attached directly to the lifting device. Alternatively, a further possible element of the holding mechanism can also be attached to the lifting device.

The rotating device can be attached to the lifting device. In particular, the first medical device can be attached directly to the rotating device. The rotating device can be designed in such a way that a first medical device attached to the rotating device can be rotated around the lifting device.

In embodiments, the rotating device can be designed as a ring, which can be adjusted in height along the lifting device. In particular, the rotating device can then be adjusted along the lifting device up to a minimum height, which is predefined by the height of the housing. Lower positions, in other words, positions of the first medical device closer to the floor, are achieved in that the first medical device is attached, for example, to a robotic actuator, which can position the first medical device lower than the minimum height. In particular, it is possible to rotate the first medical device attached to the rotating device in an angular range between 0° and 360°. In embodiments, the rotating device can rotate the first medical device in smaller angular ranges. Advantageously, the angular range covers at least 90° on the side of the lifting device, which is arranged opposite the housing of the mobile platform. In particular, the rotating device can rotate the first medical device in the clockwise direction and/or in the counterclockwise direction.

In alternative embodiments, the rotating device can be designed as a part ring or as a swivel joint. In particular, the rotating device can then be adjusted along the entire height of the lifting device. In particular, the rotating device can rotate the first medical device, for example in an angular range between 0° and 180°. Analogously to the design as a ring, in embodiments, the rotating device can rotate the first medical device in smaller angular ranges. Analogously, the rotation can be executed in the clockwise direction and/or in the counterclockwise direction.

The robotic actuator is configured in such a way that it enables a three-dimensional movement of the first medical device and positioning of the first medical device horizontally spaced apart from the housing and from the chassis, therefore. The chassis and the housing are advantageously permanently connected. The term "spaced apart from the housing" is synonymous with the term "spaced apart from the chassis" thereby. In embodiments, the first medical device can be attached directly to the robotic actuator.

In embodiments, the robotic actuator comprises at least one swivel joint and/or hinge joint. In particular, the robotic actuator can vary the horizontal distance of the first medical device from the housing by a variation of an angle of the swivel joint and/or hinge joint. The angle of the swivel joint and/or hinge joint can advantageously encompass a maximum angular range between 0° and 180°. In embodiments, the angular range can encompass a portion of the maximum angular range. The distance of the first medical device from the housing is at a maximum when the robotic actuator is extended to the maximum. In particular, in the maximum extended state, the angle of the swivel joint and/or hinge joint is the maximum angle of the angular range.

In embodiments, the robotic actuator can rotate or tilt the medical device about any desired axes. The angle of rotation is typically limited by the design of the robotic actuator and of the first medical device. For example, the angle of rotation can comprise a range between 0° and 120°. In particular, the robotic actuator can adjust the orientation of the first medical device via a rotation.

In embodiments, the robotic actuator can position the first medical device at different horizontal distances relative to the housing. In embodiments, the robotic actuator can adjust the height of a first medical device or position it. In particular, the height adjustability is dependent on the distance of the first medical device from the housing. The greater the distance of the first medical device from the housing, the lower the adjusting range in terms of height is which can be achieved with the robotic actuator. In particular, with a constant horizontal distance from the housing, the first medical device cannot be adjusted in height if the robotic actuator is extended to the maximum.

In embodiments, the robotic actuator can be attached to the lifting device, so it can be adjusted in height. In this embodiment, the first medical device can be roughly positioned in height via the lifting device. A fine adjustment of the height, the orientation and/or distance from the housing is possible via the robotic actuator.

In embodiments, the robotic actuator can be attached directly to the housing. In these embodiments the height adjustability of the first medical device is limited to the range of the robotic actuator in the correspondingly adjusted horizontal distance from the housing.

In embodiments, the robotic actuator can be attached to the rotating device.

The manipulation device comprises a robotic actuator and a gripping device. The first medical device can be received or gripped and put down by the manipulation device via the gripping device. In embodiments, the gripping device can be an automatic gripping device. Alternatively, the gripping device can also comprise a manual clamp or a tensioning mechanism or hook for hooking into the first medical device or magnets etc. In embodiments, the manipulation device can be attached, analogously to the robotic actuator, either directly to the housing, the lifting device or the rotating device.

Below, the expression "the first medical device is attached to the mobile platform" will be used synonymously with the meaning that the first medical device is attached to the at least one holding mechanism of any design.

The inventors have found that with at least one embodiment of the invention, it is possible to provide a mobile platform as the basis for a broad spectrum of medical applications. By way of at least one vertical lifting device, rotating device, robotic actuator and/or manipulation device respectively the platform can be configured such that it can cover, without restrictions, all conceivable workspaces from the floor up to beyond the height of a patient, but also specific, small workspaces, for example in the case of intervention. There are no limitations of the possible workspace within the limits due to the surrounding building, therefore. For example, dependent on the design of the first medical device, different medical image recordings such as X-ray, ultrasound, etc. are possible, therefore. In particular, medical procedures and/or medical examinations can be performed by the mobile platform.

The inventors have also found that the mobile platform of at least one embodiment can undertake, inter alia, assistance functions for the medical workflow and transport tasks. For example, the mobile platform can receive the first medical device with the gripper of the manipulation device and move it to a location at which the first medical device is needed.

In embodiments, the sensor module comprises at least one orientation sensor, which is designed to detect at least one reference point arranged in an environment of the mobile platform.

The mobile platform is coordinated or oriented in an environment by the detection of the reference point or reference marker. In other words, this means that the mobile platform can determine by way of the reference point where it is located in its environment. In other words, the mobile platform can determine its position by way of the reference point. In particular, the at least one environmental parameter comprises the at least one reference point. The at least one reference point can be designed as a fixed point within a coordinate system in which the mobile platform is oriented. The coordinate system can describe the environment of the mobile platform. The environment can be, for example, an operating theatre, a radiology department, a treatment room or an entire hospital. In particular, the orientation of the mobile platform in its environment enables defined points or locations in the environment to be approached. Defined points or locations can be within a room, on a patient couch, a park position of the mobile platform, etc.

In embodiments, a reference point can be optical or electromagnetic. Alternatively, the reference point can be at least one sound signal.

In alternative embodiments, the at least one orientation sensor determines the position of the mobile platform in the environment by way of odometry or by tracking and measurement of the environment. The position can be determined optically, inertially, acoustically or via radio.

The inventors have found that, due to the coordination or orientation of the mobile platform in the environment of the mobile platform, it is possible for the mobile platform of at least one embodiment to automatically move to a specified point or location in the environment. In other words, it is possible that the mobile platform can be moved completely autonomously. As an alternative or in addition, it is possible that the mobile platform follows specific trajectories. Trajectories can be movement paths or routes in the environment. Advantageously, trajectories can be a sequence of points or positions in the environment, which the mobile platform follows consecutively. The trajectories can be followed by the mobile platform via the chassis. Advantageously, the points of the trajectories can correspond to operating positions of the first medical device. In particular, the trajectories can be followed by the first medical device via the holding mechanism. In particular, the trajectories can be followed by the first medical device by way of guidance of the holding mechanism and simultaneous movement of the chassis.

Where a trajectory is mentioned below, this can relate to following with the chassis and/or with the at least one holding mechanism. In particular, it can relate to following with the mobile platform as a whole and following with the first medical device.

In addition, the inventors have found that for an orientation of the mobile platform of at least one embodiment by way of at least one reference point, no reconstruction measures are necessary in the environment of the mobile platform. The reference point can be adjusted to the construction and the mobile platform can orient itself in the environment on the basis of the reference point.

In embodiments, the sensor module comprises at least one collision sensor, which is designed to detect objects in the environment of the mobile platform.

Due to the detection of objects in the environment of the mobile platform, the mobile platform can be prevented from colliding with one of these objects when it moves via the chassis. The collision sensor can be designed to be, for example, optical, acoustic, electromagnetic, tactile, capacitive or aerodynamic. Objects can be, for example, walls, tables, chairs, devices, medical devices, other mobile platforms, people, etc. If an object is detected, the mobile platform either remains stationary or alternatively changes its direction of movement in order to bypass the object. In particular, the at least one environmental parameter comprises the object detected with the collision sensor.

In preferred embodiments the collision sensor can also comprise a distance sensor. Advantageously, the distance sensor is integrated in the collision sensor. In other words, the distance sensor and the collision sensor form a combined sensor. The distance sensor can be based on the same techniques (optical, acoustic, electromagnetic, tactile, capacitive or aerodynamic) as the collision sensor. With the distance sensor it is possible to purposefully move the mobile platform towards an object up to a defined distance and to stop the mobile platform before it collides with the object. In particular, the at least one environmental parameter can comprise the distance of the mobile platform from an object.

In particularly preferred embodiments, the mobile platform comprises collision sensors—and in embodiments, distance sensors in all possible directions of movement of the chassis. Advantageously, a collision in the case of any change in position/any moving of the mobile platform can be prevented in this way independently of the direction of movement of the mobile platform.

In particularly preferred embodiments, at least one collision sensor and in embodiments, at least one distance sensor is arranged on the at least one holding mechanism. In particular, it is thereby possible to prevent a collision of the first medical device with an object if the first medical device is positioned with the at least one holding mechanism. In particular, the first medical device can be moved towards a patient up to a defined distance or be positioned at a defined distance from a patient.

The inventors have found that the collision sensor of at least one embodiment serves to protect devices and people. In addition, the inventors have found that purposeful movement of the mobile platform and/or of the first medical device to a point at a defined distance from an object is possible via a distance sensor integrated in the collision sensor. For example, the first medical device can be an X-ray detector, which in this way can be moved towards a patient up to a defined distance without colliding with the patient. In particular, with the aid of the collision sensor the mobile platform can park in a parking space between other objects without colliding with them.

In addition, the inventors have found that semi-autonomous movement of the mobile platform of at least one embodiment is possible with the collision sensor and/or the orientation sensor. Semi-autonomous means that the movement is conducted by an operator, but the mobile platform automatically, for example, keeps in lane with the orientation sensor and/or avoids collisions with the collision sensor. In addition, the mobile platform can automatically move into its parking position. Alternatively, with the collision sensor and/or the orientation sensor, it is possible that the mobile platform can move completely autonomously. The mobile platform can move in any desired development between semi-autonomous to completely autonomous, therefore.

In embodiments, the sensor module comprises at least one patient detection sensor.

The patient detection sensor preferably comprises a camera with which a patient can be captured in images. In embodiments, a frame is fitted in the image of the patient to be able to allocate body regions or landmarks in the physiology of the patient. In other words, the patient detection sensor can detect body regions of a patient. With body region detection, the mobile platform can detect different body regions of the patient and spatially allocate them. In particular, the at least one environmental parameter can comprise a patient, for example captured in images. In example embodiments, the mobile platform can in a first step orient itself on at least one reference point on a patient table on which the patient is lying. Using this reference point the mobile platform can firstly follow the patient couch and at the same time detect the entire patient with the patient detection sensor. The data from this detection can, as described above, be processed further by fitting a frame. In a simplified embodiment, the patient detection sensor detects only the head and the feet of the patient and thus its orientation in the environment. In embodiments, the patient detection sensor can also detect a patient who is standing or sitting.

The inventors have found that the patient detection sensor enables autonomous positioning of the mobile platform of at least one embodiment relative to the anatomy or physiology of a patient. For example for an ultrasound examination of the abdomen of a patient, the mobile platform can position itself at a suitable location, which was determined by the mobile platform or the sensor module of the mobile platform with the patient detection sensor and the body region detection. Manual positioning of the mobile platform by a doctor is not necessary, therefore. This example can be transferred to further examinations and assistance functions. In particular, via the patient detection sensor it is possible for the mobile platform to be able to perform independent examinations on a patient. In particular, the inventors have found that the mobile platform can be oriented in the environment of the patient with the patient detection sensor on the basis of the physiology of a patient.

In embodiments of the invention, the chassis and/or the at least one holding mechanism is/are designed to adjust the operating position of the first medical device attached to the at least one holding mechanism to the movement of a second medical device.

In other words, the operating position or position of the first medical device can be adjusted to the position of the second medical device. In particular, a coordinated movement of two medical devices relative to each other is possible. In embodiments, the coordinated movement can be adjusted. In particular, the movement of the first medical device can be adjusted to the movement of the second medical device. In other words, the position of the first medical device can be adjusted to the position of the second medical device. This means, in other words, that the mobile platform and/or the first medical device detects the movement and/or the position of the second medical device. The movement or position of the second medical device can be detected, for example, via optical, tactile, thermodynamic, and/or capacitive sensors of the sensor module. In particular, the at least one collision sensor of the sensor module, which comprises the at least one distance sensor, can detect the movement of the second medical device. Alternatively, for example, the second medical device can transmit its position to the mobile platform. The mobile platform identifies the position of the second medical device relative to the position of the first medical device by way of the orientation in the room or the environment of the mobile platform, therefore. The mobile platform can position or adjust the first medical device in accordance with or as a function of the position of the second medical device, therefore. In other words, the first medical device can follow the movement or position of the second medical device, therefore. Matching the position or movement of the first medical device can be achieved via the holding mechanism and/or via the chassis of the mobile platform.

In embodiments, the mobile platform identifies a position of the second medical device at each instant. Alternatively, the mobile platform requests the position of the second medical device if required and/or regularly. The request can be executed directly between mobile platform and second medical device. Alternatively, the request can be executed via a central distribution system.

In particular, the coordination of the mobile platform or the first medical device and the second medical device with each other can be achieved via the orientation of the individual medical device in the room by the respective orientation sensor or collision sensor. The individual medical devices can determine their position with the respective orientation sensor in their shared environment, in particular in relation to a shared reference point or a shared reference coordinate system. In particular, the medical devices can transmit their respective positions directly to the other medical device in each case. Alternatively, the transfer is to a central distribution system. The distribution system then forwards the positions of the individual medical devices.

The transfer of information about the positions of the medical devices can be achieved in particular via radio.

Alternatively, an exchange with each other can be in contact via at least one sensor of the sensor modules. Alternatively, the coordination can also be achieved via the collision sensor of the mobile platform, which is designed to detect a distance or the relative position between mobile platform/first medical device and second medical device.

The coordination of the mobile platforms among themselves advantageously facilitates matching a first medical device on a mobile platform in relation to a second medical device.

Advantageously, the coordination between the mobile platform or the first medical device and second medical device also comprises an exchange about the operating positions of the medical devices, optionally as a function of a holding mechanism. Matching a first medical device on a mobile platform to a second medical device with the respective holding mechanism and/or with the respective chassis is simplified or enabled, therefore.

In example embodiments, position information, sensor information or further information can be exchanged via radio.

The second medical device can be moved or positioned or guided in different ways. In embodiments, the second medical device can be encompassed by a second mobile platform. Alternatively, the second medical device can be moved, for example by a surgeon. Alternatively, the second medical device can be supported and moved by an immobile platform. The immobile platform is permanently positioned in the environment. The immobile platform can guide a second medical device via a holding mechanism comprising a lifting device, a rotating device, a robotic actuator and/or a manipulation device. The holding mechanism of the immobile platform can be arranged on the ceiling, the floor or the wall of a room. Further embodiments relating to the immobile platform follow in the further description.

In embodiments, the movement or position of the second medical device can be adjusted to the movement or position of the first medical device.

In embodiments, the first and the second medical devices can each follow a defined trajectory. In particular, this trajectory can be defined by a user in advance. Alternatively, the trajectory can be automatically defined in advance, for example as a function of a planned examination. Alternatively, the trajectory can be instantaneously determined from at least one environmental parameter via at least one sensor of the sensor module of the mobile platform and be automatically stipulated such that, for example, defined body regions of a patient are followed by way of the trajectory.

The inventors have found that an automated examination procedure on a patient is made possible by matching a first medical device to a second medical device.

In one example embodiment, the first medical device can be designed as an X-ray detector and the second medical device as an X-ray tube. The X-ray tube can be attached to an immobile platform. In particular, the position or movement of the X-ray detector can be adjusted to the position or movement of the X-ray tube. Alternatively, the position or movement of the X-ray tube can be adjusted to the position or movement of the X-ray detector. In particular, a plurality of X-ray records can be automatically taken along a trajectory, therefore, analogously, for example, to a C-arm image or a sectional image.

In an alternative example embodiment, the first medical device is designed as a work light. The second medical device can be guided by a surgeon's hand. The second medical device can be, for example, a scalpel. Advantageously, the position or movement of the work light can be adjusted to every movement of the surgeon's hand or of the scalpel. This can facilitate the workflow during an operation since no manual adjustment of the work light is necessary.

In alternative embodiments, the first medical device is designed as an interventional platform. The second medical device is designed as an angiography system, in particular as a C-arm, particularly preferably as an X-ray radiation source or X-ray detector. The second medical device can also be designed as a patient table on which the patient lies during the procedure. The movement or the position of the interventional platform or the holding mechanism in the form of a robotic actuator can accordingly be adjusted to a displacement movement of the angiography system and/or of the patient table necessary for image data acquisition. In particular, a position or a movement trajectory for a guide catheter, guide wires, balloon implants or stent implants can be adjusted accordingly, synchronized with the second medical device, therefore. In this way, the interventional procedure can be optimized with monitoring of the imaging.

A movement of the second medical device can also be monitored via a sensor unit of the mobile platform to rule out collisions with the second medical device. Furthermore, for example for the example embodiment of the interventional platform, an evasion of the first medical device or the mobile platform can also be made possible in order to enable steeper angulations of the angiography system or to guarantee unrestricted access to the patient in emergencies.

In embodiments of the invention, the mobile platform comprises at least two holding devices. The holding devices are each designed for guiding a first and a third medical device. The holding devices are also configured to position the first and the third medical device respectively within one adjusting range respectively in at least one operating position respectively.

In particular, the third medical device can be designed as the second medical device, which is arranged on the mobile platform. In this embodiment, the first medical device on the platform is adjusted via the corresponding holding mechanism to the movement of the third medical device. In particular, the third medical device can follow a predefined or pre-planned trajectory. In other words, the third medical device can be guided along the trajectory by the corresponding holding mechanism. In particular, the trajectory can be specified by a user. Alternatively, the mobile platform can instantaneously calculate the trajectory of the third medical device using the patient detection or the orientation in the room. Alternatively, the trajectory can be instantaneously calculated from at least one reference point, which is arranged, for example in the environment, on the patient, on the patient table, etc. Alternatively, the trajectory can be instantaneously calculated by the mobile platform from image data. The image data is preferably acquired with one of the two medical devices or a further medical device on a different mobile or immobile platform.

Alternatively, the second and the third medical device can be different. In particular, the second medical device can be attached to a further mobile platform or to an immobile platform. Alternatively, the second medical device can be moved manually. The first and the third medical devices can both be adjusted to the movement of the second medical device.

Advantageously, the holding mechanism of the first and of the third medical device can comprise partially shared components. In the case of a partially shared holding mechanism, at least one of the components or elements of the holding devices of the first and of the second medical device is designed for guiding the two medical devices.

In example embodiments, the first and the third medical device can be attached to one robotic actuator respectively. In particular, the two robotic actuators can be attached to a shared lifting device. Alternative embodiments of a partially shared holding mechanism of the first and of the second medical device are conceivable.

In example embodiments, the first medical device can be an X-ray detector and the third medical device an X-ray tube. The holding devices of the X-ray detector and the X-ray tube can be designed in such a way that the X-ray tube and the X-ray detector can move around a patient in a pre-planned trajectory. In this way, as in the case of a C-arm record, X-ray records can be taken from different perspectives of the patient.

The inventors have found that guiding or moving or positioning two medical devices on a shared mobile platform has the advantage that the two medical devices can be moved stably relative to each other since they have a shared reference point with the mobile platform. No further orientation in the room is necessary for this. Errors in the spatial orientation of the platform have no effect on the relative movement of the two medical devices, which are attached to a shared mobile platform. In addition, the space requirement is lower when two medical devices are attached to a shared mobile platform than when two medical devices are attached to one individual mobile platform respectively.

In embodiments of the invention, the mobile platform comprises a battery module. The battery module serves to supply the mobile platform with energy, in particular the drive unit for the chassis, but also the motor function for the holding mechanism, etc. Advantageously, the battery module does not restrict the mobility of the mobile platform. In particular, the battery module can be arranged fully on the chassis of the mobile platform. In particular, the battery module does not require any further permanent components, which are arranged outside of the mobile platform or in the environment of the mobile platform, such as, for example, cables.

Advantageously, the battery module is chargeable. In particular, it is possible to charge the battery module when the mobile platform is not needed. For example, the battery module can charge at night or when a different mobile platform can fulfil the task of the mobile platform.

Alternatively, the mobile platform can be supplied with energy by way of flexible cable solutions, cable-free energy transfer such as induction or alternative inbuilt storage solutions such as fuel cells.

The inventors have found that the use of a battery module enables flexible deployment of the mobile platform. Advantageously, no permanent external components such as cables are required for a battery module, which can restrict the mobility of the mobile platform and increase the risk of injury to the patient and operator due to trip hazards.

In embodiments of the invention, the mobile platform comprises an anti-tilt mechanism.

The anti-tilt mechanism is used in particular so that the mobile platform does not tilt or fall over even when the first and/or third medical device is positioned with the holding mechanism in an operating position horizontally remote from the center of gravity of the mobile platform.

The anti-tilt mechanism can be formed, in particular, by a low-lying center of gravity of the mobile platform. A low-lying center of gravity is arranged as low down as possible inside the mobile platform. In other words, a low-lying center of gravity is arranged on the chassis of the mobile platform as close as possible to the floor.

Alternatively or in addition, the anti-tilt mechanism can be formed by a large base area. A large base area means that the chassis of the mobile platform comprises a large area. The size of the base area must not restrict the mobility or maneuverability of the mobile platform, however.

In example embodiments, the weight of the mobile platform can serve as the anti-tilt mechanism. For this, the mobile platform has to be designed to be sufficiently heavy such that the weight of the mobile platform can compensate the lever action due to a first and/or third medical device attached to the mobile platform.

In example embodiments, the anti-tilt mechanism can comprise at least one acceleration sensor in the sensor module, which detects tilting of the mobile platform and automatically prevents it with a compensation movement of the at least one holding mechanism. For example, the acceleration sensor can detect oblique movements of the mobile platform or movements, which do not occur during normal use of the mobile platform. In particular, on detection of such a movement of the mobile platform, the acceleration sensor can forward this information to the holding mechanism. In particular, the motion sensor can forward information about the direction of this movement of the mobile platform to the holding mechanism. The holding mechanism can shift the center of gravity of the mobile platform counter to the tilting movement by way of a movement of the first medical device. Shifting the center of gravity can prevent tilting of the mobile platform.

Alternatively, the anti-tilt mechanism can comprise specified conditions, which define how far away from the center of gravity of the mobile platform in the horizontal direction a first and/or third medical device may be positioned with the at least one holding mechanism so the mobile platform does not tilt. This condition can depend on the weight and the embodiment of the first and/or third medical device.

In particular, the adjusting range, which the at least one holding mechanism comprises, determines the design of the anti-tilt mechanism. The bigger the radius of movement of the adjusting range, in other words, the further away the first and/or third medical device can be positioned with the at least one holding mechanism horizontally from the center of gravity of the mobile platform, the more stable the anti-tilt mechanism has to be.

The inventors have found that the risk that the mobile platform of at least one embodiment will tilt can be minimized, in particular as a result of a low-lying center of gravity and/or a large base area of the mobile platform. Advantageously, the size of the base area of the mobile platform is limited in such a way that it fits through a door. In particular, the base area can comprise, for example, an area of 80 cm×80 cm. The weight of such a platform without the first medical device can be, for example, 80 kg. In addition, the inventors have found that the embodiment of the anti-tilt mechanism is advantageously dependent on the first and/or third medical device, which is attached to the mobile platform, and on the radius of movement of the holding mechanism.

In embodiments of the invention, the mobile platform comprises a shelf space. In particular, the top of the housing of the mobile platform can be designed as a shelf space. Advantageously, no additional components are necessary for the embodiment of the shelf space. Advantageously, the shelf space is at table height, so it can be used by the operator and/or the patient for depositing items. Advantageously, the shelf space is designed in such a way that it can be easily disinfected. Advantageously, the shelf space is exactly the same size as the base area of the mobile platform. The shelf space does not increase the space requirement of the mobile platform, therefore.

The inventors have found that the convenience for the operator and/or the patient is increased by way of the embodiment of the top of the housing of the mobile platform as a shelf space. In particular, the range of motion of the mobile platform is not restricted by additional structures, which are intended to serve as a shelf space. The mobile platform can be flexibly moved or positioned as close as possible to a patient or an item without being restricted by a structure, which is intended to serve as a shelf space.

In embodiments of the invention, the chassis of the mobile platform is omnidirectional. Omnidirectional means that the mobile platform can be moved with the chassis in any direction independently of the orientation of the mobile platform.

The omnidirectional chassis can comprise at least one roller, which can roll in any direction. In particular, the at least one roller can be spherical in design.

Alternatively, the chassis can comprise at least one wheel. The at least one wheel is advantageously connected by a swivel joint to the housing of the mobile platform.

Advantageously, the swivel joint is designed to rotate about a vertical axis.

Advantageously, the chassis comprises at least four rollers or wheels. Advantageously, the four rollers or wheels are arranged in a square or rectangle.

Alternatively, the chassis can be designed as an air cushion.

The inventors have found that the movement of the mobile platform of at least one embodiment is configured to be maximally flexible via omnidirectional chassis. Due to the omnidirectional chassis, no maneuvering is necessary as with a car if the mobile platform is to be moved into a particular position since the mobile platform can be moved at any time in any direction via the omnidirectional chassis. The inventors have found that this leads to time savings and that the space requirement of the mobile platform is lower since no space has to be provided for maneuvering the mobile platform. In addition, the inventors have found that a working space of the mobile platform can be increased due to the omnidirectional chassis. The working space comprises all operating positions of the first and/or third medical device. In particular, flexible movement in any direction before, after or during an examination is possible via the omnidirectional chassis. This enables the omnidirectional chassis to follow any trajectories.

According to a further embodiment, the invention relates to a system, which comprises a plurality of inventive mobile platforms of at least one embodiment. The plurality of inventive mobile platforms is coordinated among themselves. In particular, one mobile platform from the plurality of mobile platforms can be moved relative to the position or movement of a different mobile platform from the plurality of mobile platforms.

Advantageously, the one mobile platform knows the position of the other mobile platform at any point in time. Alternatively, the one mobile platform requests the position of the other mobile platform if required and/or regularly. The request can be executed directly between the mobile platforms. Alternatively, the request can be executed by a central distribution system.

In particular, this coordination of the plurality of mobile platforms among themselves can be formed by way of the orientation of the individual mobile platforms in the room by the respective orientation sensor. The individual mobile platforms of the plurality of mobile platforms can determine their position in their environment with the respective orientation sensor. In particular, the mobile platforms can communicate their respective positions directly to a different platform of the plurality of mobile platforms. Alternatively, the mobile platforms communicate their respective positions to a central distribution system. The distribution system forwards the positions of the individual mobile platform of the plurality of mobile platforms to the other mobile platforms respectively of the plurality of mobile platforms.

The transfer of information about the positions of the plurality of mobile platforms can be achieved, in particular, via radio. Alternatively, the mobile platforms of the plurality of mobile platforms can be in contact with each other via at least one sensor of the sensor module. In example embodiments, a mobile platform can determine the distance from another mobile platform from the plurality of mobile platforms with at least one ultrasound sensor.

The coordination of the mobile platforms among themselves advantageously facilitates the matching of a first medical device on a mobile platform from the plurality of mobile platforms to a second medical device on another mobile platform from the plurality of mobile platforms. This means that the first medical device is attached with one holding mechanism to one mobile platform and the second medical device is attached with a different holding mechanism to a different mobile platform. In particular, the first medical device can be adjusted to the second medical device or the second medical device to the first medical device.

Advantageously, the coordination of the plurality of mobile platforms also comprises an exchange about the operating positions of the medical devices attached to the individual mobile platforms as a function of the respective holding mechanism. Matching a first medical device on a mobile platform from the plurality of mobile platforms to a second medical device on a different mobile platform from the plurality of mobile platforms with the respective holding mechanism and/or with the respective chassis is simplified or enabled, therefore.

In example embodiments, the mobile platforms of the plurality of mobile platforms can exchange further information in particular via radio. In particular, the mobile platforms can exchange information about which medical device is assembled on the respective mobile platform from the plurality of mobile platforms. In particular, the mobile platforms can exchange information about the assignment plan or usage plan of each individual mobile platform from the plurality of mobile platforms. The assignment plan can comprise information as to when the respective mobile platform is required where and when it has free times and/or when it needs to charge its battery module, etc. In this way, the operating time of the plurality of mobile platforms can be optimally utilized. The operating time of the mobile platforms is the time when a mobile platform can be used for medical examinations, medical procedures and/or assistance functions. In addition, a charging station does not have to be provided for every mobile platform of the plurality of mobile platforms for example. The plurality of mobile platforms can compare their charge status among themselves and optimally determine the charging times.

The exchange of information between the mobile platforms is referred to as the communications structure.

The inventors have found that a communications structure between a plurality of inventive mobile platforms of at least one embodiment can optimize the performance of medical examinations or medical procedures or assistance functions in which the spatial coordination between two or more mobile platforms is necessary. In addition, the entire workflow, aided by the plurality of mobile platforms in a hospital, a hospital department or a doctor's surgery can be optimized in this way.

In embodiments of the invention, the system comprises at least one immobile platform without chassis, which is coordinated with the plurality of inventive mobile platforms.

Like the mobile platform, an immobile platform can comprise at least one holding mechanism for guiding a medical device. This at least one holding mechanism can be designed in such a way that it can position a medical device in an operating position within an adjusting range. In particular, the immobile platform cannot be freely moved in its environment. Advantageously, the holding mechanism of the mobile platform is attached to a ceiling, a floor or a wall of the environment of the immobile platform. The environment of the immobile platform can be, for example, a radiology department, an operating theatre, etc. In particular, the at least one holding mechanism of the immobile platform can be moved on a system comprising at least one guide element. Advantageously, the guide element(s) is/are designed as rails. Advantageously, the rails are arranged on the ceiling, wall or floor. Advantageously, the at least one holding mechanism can be moved or positioned along the rails in at least one dimension.

The plurality of mobile platforms can exchange information with the at least one immobile platform, as described above for the plurality of mobile platforms, and is coordinated with the immobile platform. In this way, the movement or position of a first medical device on a mobile platform from the plurality of mobile platforms can be adjusted to the movement or position of a second medical device on the immobile platform. In particular, the movement or position of a second medical device on the immobile platform can be adjusted to the movement or position of a first medical device on a mobile platform from the plurality of mobile platforms.

In particular an X-ray tube can be attached to the at least one holding mechanism of the immobile platform. The X-ray tube can be positioned in an operating position within the adjusting range of the at least one holding mechanism of the immobile platform and/or can follow a trajectory comprising a plurality of operating positions. Advantageously, a mobile platform from the plurality of mobile platforms comprises an X-ray detector. In particular, the movement or position of the X-ray detector on the mobile platform can be adjusted to the movement or position of the X-ray tube on the immobile platform. Alternatively, the movement or position of the X-ray tube can be adjusted to the movement or position of the X-ray detector.

The inventors have found that the system comprising at least one mobile platform of at least one embodiment and at least one immobile platform is advantageous since there are already immobile platforms in medical institutions, such as hospitals and/or doctor's surgeries, which are advantageously coordinated with the plurality of mobile platforms. In particular, there are medical devices, which, for example owing to the high energy requirement, cannot be attached to mobile platforms since they cannot be operated via a battery module. In particular, coordination of such medical devices on immobile platforms with medical devices on mobile platforms is advantageous.

FIG. 1 shows a view of an example embodiment of an inventive mobile platform 1 for the automatic performance of ultrasound examinations. The mobile platform 1 comprises a holding mechanism 12 and an omnidirectionally movable chassis 13. The housing 131 of the mobile platform 1 is designed in such a way that it comprises a shelf space 14 at table height. The holding mechanism 12 comprises a lifting device 121, which protrudes beyond the shelf space 14, a rotating device 122 attached to the lifting device 121 and which is designed to rotate above the shelf space 14 about the holding mechanism 121, and a robotic actuator 123 attached to the rotating device 122. Depending on the application, the lifting device 121, rotating device 122, robotic actuator 123 and/or, in alternative embodiments, manipulation device 124 can be designed in such a way that they can automatically cover the entire adjusting range on the patient from head to toe. This applies to all example embodiments shown in the following figures. The floor-based omnidirectional chassis 13 and the holding mechanism 12 are oriented in the same spatial coordinate system. In particular, movements of chassis 13 and holding mechanism 12 that are coordinated with each other can be executed, therefore. This applies to all example embodiments shown in the following figures. An ultrasound head 4 is attached to the robotic actuator 123. Further ultrasound heads 4' for replacement are arranged at the side of the shelf space 14 of the mobile platform 1.

In alternative embodiments the holding mechanism 12 can comprise a manipulation device 124 instead of a robotic actuator 123. The manipulation device 124 can automatically grasp the ultrasound head 4, 4' that is appropriate for a corresponding examination. In the case of a robotic actuator 123, an operator of the device has to attach the appropriate ultrasound head 4, 4' to the robotic actuator 123. A monitor 5 for displaying the image data of the ultrasound examination is arranged on the shelf space 14 of the mobile platform 1. In particular, an input device 6 for the ultrasound device is arranged on the shelf space 14 of the mobile platform 1, with which input device suitable parameters can be set for the examination and the display. The mobile platform 1 is in front of a patient couch 2 on which a patient 31 is lying. The mobile platform 1 can detect the abdominal area of the patient 31 with the patient detection sensor and the body region detection and automatically perform an ultrasound examination in the abdominal area. The mobile platform 1 can change or adjust its position in the environment at any time with the chassis 13. In particular, the mobile platform 1 can automatically position itself for performing an ultrasound examination.

Figure 2:
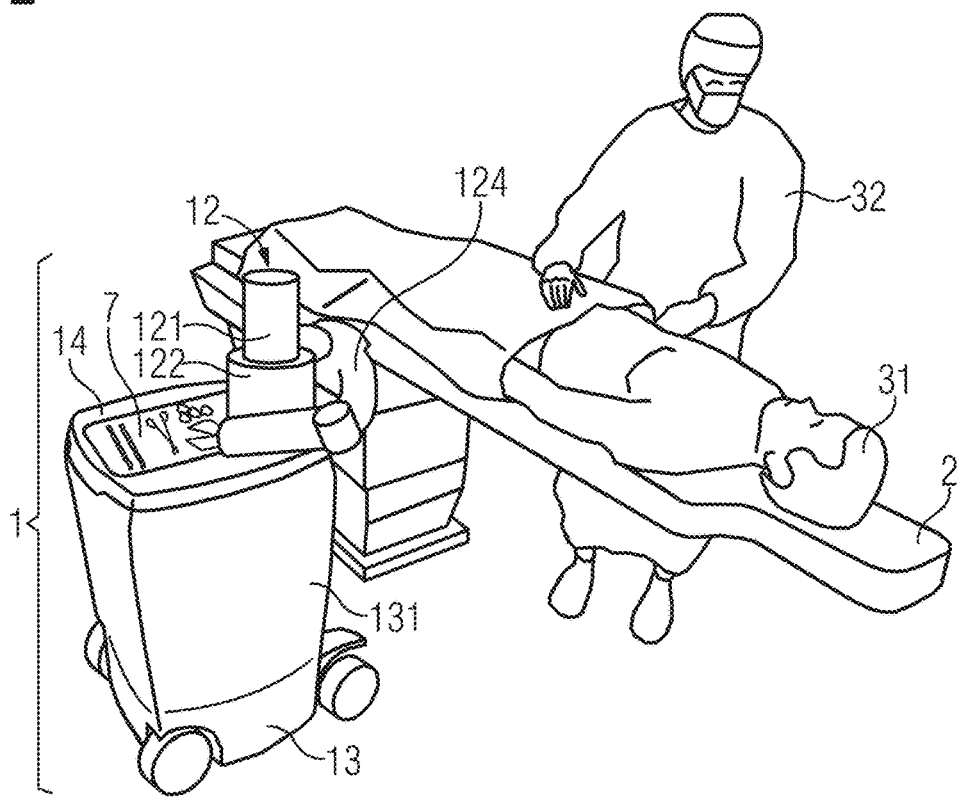
FIG. 2 shows a view of an example embodiment of an inventive mobile platform for the performance of assistance functions.

FIG. 2 shows a view of an example embodiment of an inventive mobile platform 1 for the performance of assistance tasks. In particular, the mobile platform 1 is designed to assist medical workflows. The holding mechanism 12 of the mobile platform 1 has a design similar to the holding mechanism 12 in FIG. 1.

In contrast to the holding mechanism 12 in FIG. 1, the holding mechanism 12 here comprises a manipulation device 124 instead of a robotic actuator 123. The mobile platform 1 is positioned in front of a patient couch 2 on which a patient 31 is lying. An operator or a user 32 of the mobile platform 1 stands on the other side of the patient couch 2. The operator or user 32 of the mobile platform 1 is a doctor or a medical professional here, who carries out an examination on the patient 31. A large number of small medical devices 7, such as, for example, medical instruments and/or medical materials and/or an endoscope and/or a work light, is arranged on the shelf space 14 of the mobile platform 1. The mobile platform 1 can receive a small medical device 7 from the shelf space 14 via manipulation device 124 and pass it to the operator or user 32 for the examination and/or treatment of the patient 31.

Figure 3:
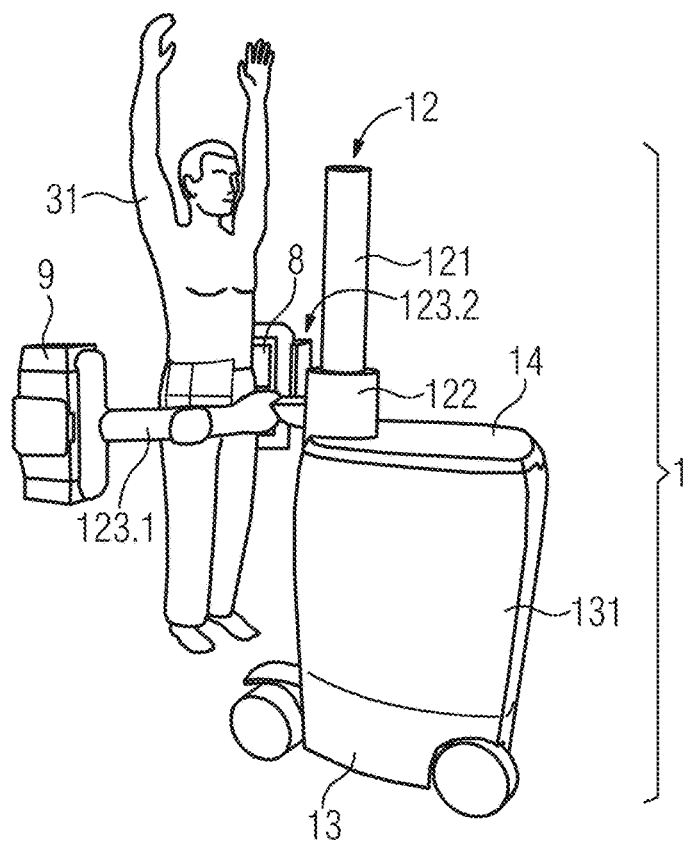
FIG. 3 shows a view of an example embodiment of an inventive mobile platform comprising two medical devices on a partially shared holding mechanism.

FIG. 3 shows a view of an example embodiment of an inventive mobile platform 1 comprising two medical devices 8, 9 on a partially shared holding mechanism 12. The mobile platform 1 is designed for automatically taking X-ray records of a patient 31. The holding mechanism 12 of the mobile platform 1 has a design similar to the holding mechanism 12 in FIG. 1.

In contrast to the holding mechanism 12 in FIG. 1, the holding mechanism 12 here comprises two robotic actuators 123.1, 123.2 instead of one robotic actuator 123, and these are attached to the same rotating device 122. In the view in FIG. 3, the rear robotic actuator 123.2 is hidden by other components of the mobile platform 1. An X-ray tube 9 is attached to the front robotic actuator 123.1. An X-ray detector 8 is attached to the rear robotic actuator 123.2. The X-ray detector 8 and the X-ray tube 9 are oriented horizontally to each other. Other orientations, such as, for example a vertical orientation of the X-ray tube 9 and of the X-ray detector 8, can be set with the robotic actuators 123.1, 123.2.

In the example embodiment shown, a patient 31 is positioned between the X-ray detector 8 and the X-ray tube 9. For following a trajectory, which comprises a small angular range of around 10° about a patient, the mobile platform 1 can rotate the X-ray detector 8 and the X-ray tube 9 about the patient 31 via rotating device 122. For following a trajectory, which covers a greater angular range than 10° about the patient, the complete mobile platform 1 can be moved around with the omnidirectionally movable chassis 13 about the patient 31 to take X-ray records from different angles.

In particular, a circular trajectory can be followed in this way whose center is the patient 31. In addition, the arrangement of the X-ray detector 8 and the X-ray tube 9 with the lifting device 121 can be adjusted in height. This is necessary, in particular, if a region of the patient 31 is to be recorded which is greater than the vertical extent of the X-ray detector 8. A vertical scan of the patient 31 can be created due to the height adjustability of the X-ray detector 8 and the X-ray tube 9. In particular, the height adjustability of the X-ray detector 8 and the X-ray tube 9 is advantageous for the adjustment of the record height to the patient's height. The settings for the height and the angle, in which the X-ray record of the patient 31 is to be taken, can be automatically determined by the mobile platform 1 with the patient detection sensor and the body region detection.

In particular, the trajectory, which, for example, has to be followed around the patient 31 for a plurality of records from different angles, can be determined with the patient detection sensor and the body region detection. Alternatively, the trajectory can be pre-set, for example if all patients to be examined are positioned at a pre-defined position and the mobile platform 1 can follow the trajectory relative to the environment. In particular, any trajectory around the patient 31 can be followed by way of simultaneous displacement of the mobile platform 1 with the chassis 13 and movement of the X-ray tube 9 and of the X-ray detector 8.

Determination of the suitable position of the mobile platform 1 for a medical examination with the patient detection sensor has the advantage that examinations can be performed directly in the patient's room and the patient 31 no longer has to be transported for the examination. The patient 31 does not have to adopt a defined position for the examination with the mobile platform 1. In particular, an operator 32 is not required in situ since the mobile platform 1 is oriented in the room with the orientation and collision sensors and can automatically perform examinations with the aid of the patient detection sensor.

Figure 4:
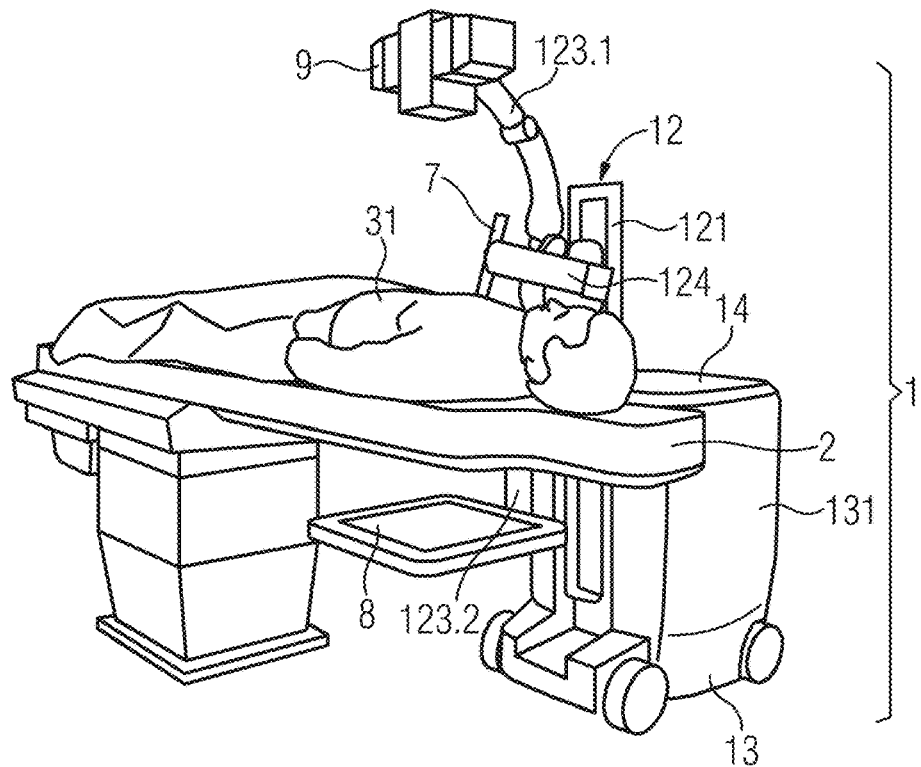
FIG. 4 shows a view of an example embodiment of an inventive mobile platform comprising three medical devices on a partially shared holding mechanism.

FIG. 4 shows a view of an example embodiment of an inventive mobile platform 1 comprising three medical devices 7, 8, 9, which are arranged on a partially shared holding mechanism 12. The mobile platform 1 is designed for performing medical procedures. The mobile platform 1 shown comprises a holding mechanism 12 and an omnidirectionally movable chassis 13. The housing 131 of the mobile platform 1 is designed in such a way that it comprises a shelf space 14 at table height.

The holding mechanism 12 comprises a lifting device 121, which protrudes beyond the shelf space 14, two robotic actuators 123.1, 123.2 and a manipulation device 124. The robotic actuators 123.1, 123.2 and the manipulation device 124 are attached to the same lifting device 121. An X-ray detector 8 is attached to the lower robotic actuator 123.2. An X-ray tube 9 is attached to the upper robotic actuator 123.1. A small medical device 7 can be grasped with the manipulation device 124. The mobile platform 1 is positioned in front of a patient couch 2 on which a patient 31 is lying. The mobile platform 1 is oriented in the room by way of the reference points in the environment and/or on the patient couch 2 in such a way that it can purposefully control a position on the patient couch 2.

With the patient detection sensor and the body region detection the mobile platform 1 can detect the body region of the patient 31 in which the treatment is to be performed. The mobile platform 1 takes X-ray images of the corresponding body region of the patient 31 with the X-ray detector 8 and the X-ray tube 9. The mobile platform 1 can coordinate the movement or guiding of the small medical device 7 by way of the manipulation device 124 with this image data from the X-ray record. The image data is therefore used for the coordination of the small medical device 7 in relation to the mobile platform 1 and thus enables, in particular, a fine coordination of the movement of the manipulation device 124 on the basis of the image data. In this way, medical procedures can be performed automatically via the mobile platform 1. In particular, the position of the medical device 7, 8, 9 can be adjusted to the movement of the patient 31 or the organs of the patient 31.

Figure 5:
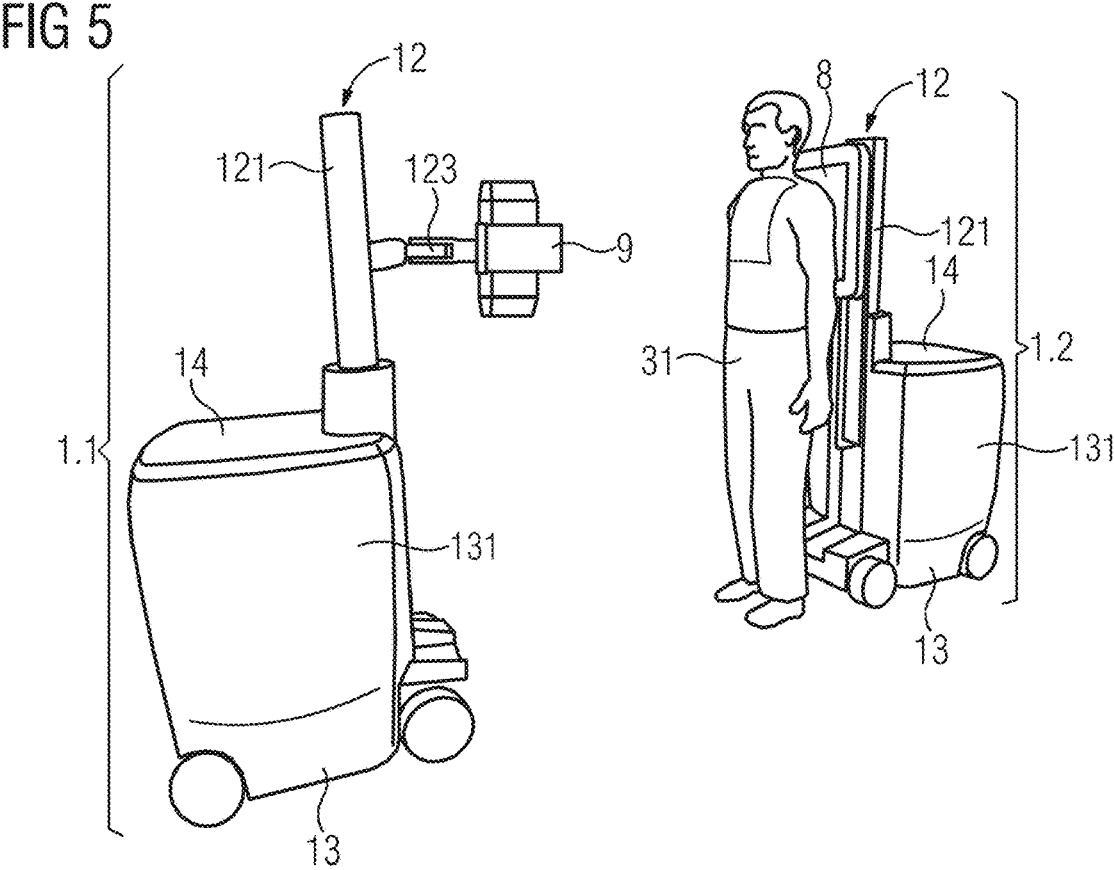
FIG. 5 shows a view of an example embodiment of a system comprising two inventive mobile platforms for automatically taking an X-ray record.

FIG. 5 shows a view of an example embodiment of a system comprising two inventive mobile platforms 1.1, 1.2, which are designed for automatically taking an X-ray record. In alternative embodiments, the system can comprise more than two mobile platforms. The mobile platforms 1.1, 1.2 each comprise an omnidirectionally movable chassis 13 and a housing 131, which is designed in such a way that it comprises a shelf space 14 at table height.

The first mobile platform 1.1 also comprises a holding mechanism 12, which comprises a lifting device 121 and a robotic actuator 123 attached to the lifting device 121. An X-ray tube 9 is attached to the robotic actuator 123.

The second mobile platform 1 also comprises a holding mechanism 12, which comprises a lifting device 121. An X-ray detector 8 is attached to the lifting device 121.

The two mobile platforms 1.1, 1.2 are coordinated with each other in the environment. In addition, the mobile platforms 1.1, 1.2 can detect a patient 31 with the respective patient detection sensors and the body region detection and automatically position the X-ray tube 9 and the X-ray detector 8 in such a way that an X-ray record of the body region of a patient 31 pre-set by an operator can be taken. The positioning of the X-ray tube 9 and the X-ray detector 8 can be carried out for patients 31 of any height and for any position of the patient 31 since the system of mobile platforms 1.1, 1.2 is coordinated among themselves and in the environment with orientation, collision and patient detection sensors.

The two mobile platforms 1.1, 1.2 can follow trajectories so as to be coordinated with each other for taking a plurality of X-ray records, for example similar to with a C-arm. In embodiments, the trajectory can be specified in advance by an operator 32. Alternatively, the mobile platforms 1.1, 1.2 can determine the trajectory with the sensors of the respective sensor module. The trajectory can be followed relative to the patient position or, if all patients 31 are always positioned in the same position, relative to the environment. The trajectory can be followed by the respective chassis 13. Alternatively or in addition, the trajectory can be a trajectory of the X-ray tube 9 and of the X-ray detector 8. This trajectory can be followed by the respective holding mechanism 12. In embodiments, the trajectory can be followed by the chassis 13 and the holding devices 12 in combination.

In particular, the trajectory of just one of the two mobile platforms 1.1, 1.2 can be specified or can be determined by one of the two mobile platforms 1.1, 1.2. The other mobile platform 1.1, 1.2 can be adjusted to the movement of the one mobile platform 1.1, 1.2. For this, the other mobile platform 1.1, 1.2 can detect the movement of the one mobile platform 1.1, 1.2 with the sensors of its sensor unit. Alternatively, the two mobile platforms 1.1, 1.2 can exchange their data about their respective position in the environment and the position of the medical device such as the X-ray tube 9 or the X-ray detector 8 on the respective holding mechanism 12 of the mobile platform 1.1, 1.2. The exchange of positions can be executed directly between the two mobile platforms 1.1, 1.2 or via a central distribution system.

For such applications, for example in X-ray imaging in which X-ray tube 9 and X-ray detector 8 are arranged on two mobile platforms 1.1, 1.2, as in the example embodiment shown in this figure or, if medical devices 7, 8, 9 attached to holding devices 12 collaborate in a medical procedure, two or more mobile platforms 1.1, 1.2 can position themselves relative to each other with submillimeter accuracy. In embodiments, this can be achieved by the distance and/or position information transmitted directly via radio between the mobile platforms 1.1, 1.2. Alternatively, positioning of the mobile platform 1.1, 1.2 can be achieved via reference points in the environment of the mobile platforms 1.1, 1.2. The reference points are acquired by the respective orientation sensors of the mobile platforms 1.1, 1.2. The mobile platforms 1.1, 1.2 can be coordinated via the reference points in the same environment, therefore. The mobile platforms 1.1, 1.2 are indirectly also coordinated among themselves, therefore.

Figure 6:
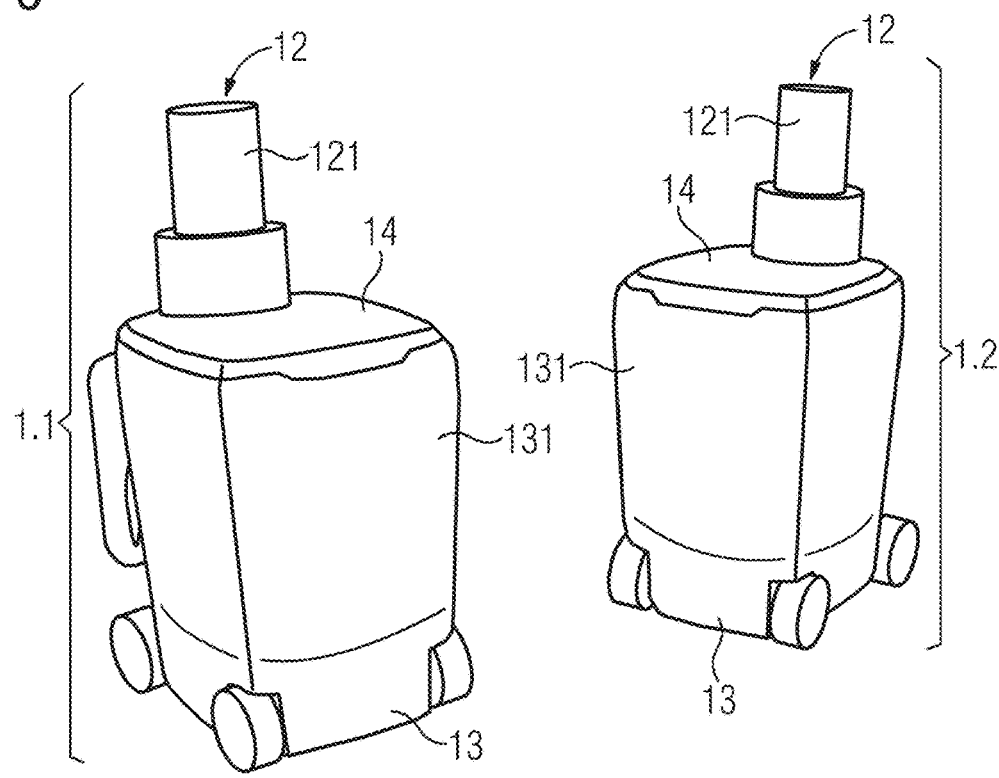
FIG. 6 shows a view of an example embodiment of a system comprising two inventive mobile platforms, wherein the mobile platforms are oriented in their environment.

FIG. 6 shows a view of an example embodiment of a system comprising two inventive mobile platforms 1.1, 1.2, wherein the mobile platforms 1.1, 1.2 are oriented in their environment. In alternative embodiments, the system can comprise more than two mobile platforms. The two mobile platforms 1.1, 1.2 can move in their environment in a coordinated manner. The two mobile platforms 1.1, 1.2 respectively comprise an omnidirectionally movable chassis 13 and respectively a housing 131. The housings 131 are designed in such a way that they each form a shelf space 14 at table height. The holding devices 12 of the two mobile platforms 1.1, 1.2 each comprise a lifting device 121, which is telescopic. This means the lifting devices 121 can be moved or pushed inside each other to save space in terms of height. For moving in the environment, for example for changing rooms in a hospital, the lifting devices 121 can thus be pushed inside each other to save space.

The two mobile platforms 1.1, 1.2 are coordinated with each other. In addition, each of the mobile platforms 1.1, 1.2 is coordinated in the environment. In this way, the mobile platforms 1.1, 1.2 can automatically position themselves in their environment, for example a hospital or a hospital department or a doctor's surgery. Positioning is dependent on the location at which they are required for a medical examination or a medical procedure or assistance functions. In addition, the mobile platforms 1.1, 1.2 can assume transport functions and bring material and/or devices into a room in which it is/they are required. The material and the devices can be, in particular, a small medical device 7 such as an endoscope, a work light, a medical instrument or medical material.

The sensor module with sensors for position determination or orientation in the room (with odometry, tracking and measurement in the room-optically, inertially, acoustically or via radio) and with sensors for detection and avoidance of collisions enables the assisted, autonomous or semi-autonomous movement of the mobile platforms 1.1, 1.2 within the environment of the mobile platforms 1.1, 1.2, for example within a workspace or in whole buildings. Depending on the requirement, the position accuracy is accurate to the centimeter in the case of transportation between workspaces or rooms or accurate to the submillimeter in the case of precise imaging applications or therapeutic applications.

Figure 7:
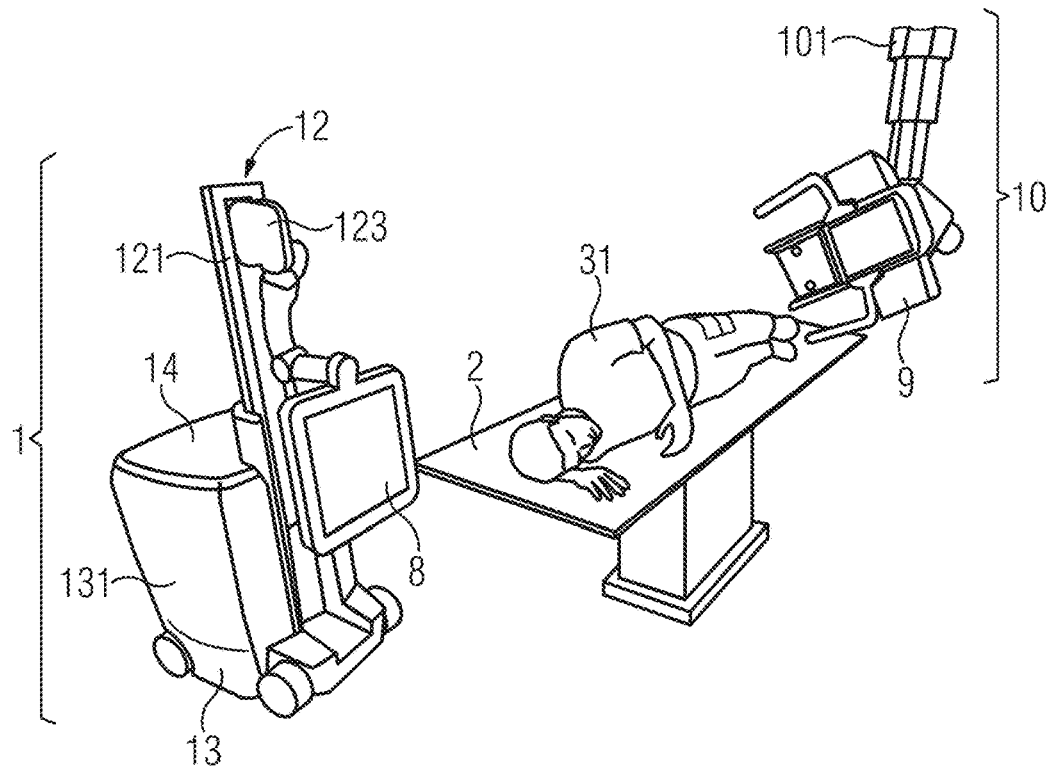
FIG. 7 shows a view of an example embodiment of a system comprising a mobile platform and an immobile platform for performing an X-ray examination on a patient.

FIG. 7 shows a view of an example embodiment of a system comprising a mobile platform 1 and an immobile platform 10 for performing an X-ray examination on a patient 31. In alternative embodiments, the system can comprise more than one mobile platform and/or more than one immobile platform. The mobile platform 1 comprises an omnidirectionally movable chassis 13 and a housing 131. The housing 131 is designed in such a way that it forms a shelf space 14 at table height. The mobile platform 1 also comprises a holding mechanism 12, which comprises a lifting device 121 and a robotic actuator 123 attached to the lifting device 121. An X-ray detector 8 is attached to the robotic actuator 123.

The immobile platform 10 comprises a holding mechanism 101, which in this example embodiment is attached to the ceiling. Alternatively, the holding mechanism 101 of the immobile platform 10 can also be attached to the floor or a wall of the room in which the immobile platform 10 is located. The holding mechanism 101 of the mobile platform 10 in this example embodiment corresponds to a robotic actuator 123. An X-ray tube 9 is attached to the holding mechanism 101 of the immobile platform 10. The mobile platform 1 and the immobile platform 10 are coordinated with each other. In particular, the X-ray tube 9 of the immobile platform 10 and the X-ray detector 8 of the mobile platform 1 are also coordinated with each other thereby. A patient table 2 is positioned in the environment of the immobile platform 10, so X-ray records of a patient 31 lying on the patient table 2 can be taken with the X-ray tube 9 and the X-ray detector 8. The X-ray detector 8 of the mobile platform 1 is adjusted to the movement of the X-ray tube 9 of the immobile platform 10 in such a way that the X-ray detector 8 can take X-ray records corresponding to the orientation of the X-ray tube 9 relative to the patient 31. Any trajectory for taking X-ray images can be followed, therefore due to simultaneous or individual moving of the mobile platform 1 by way of the chassis 13, of the X-ray detector 8 with the holding mechanism 12 and the X-ray tube 9 with the holding mechanism 101.

Figure 8:
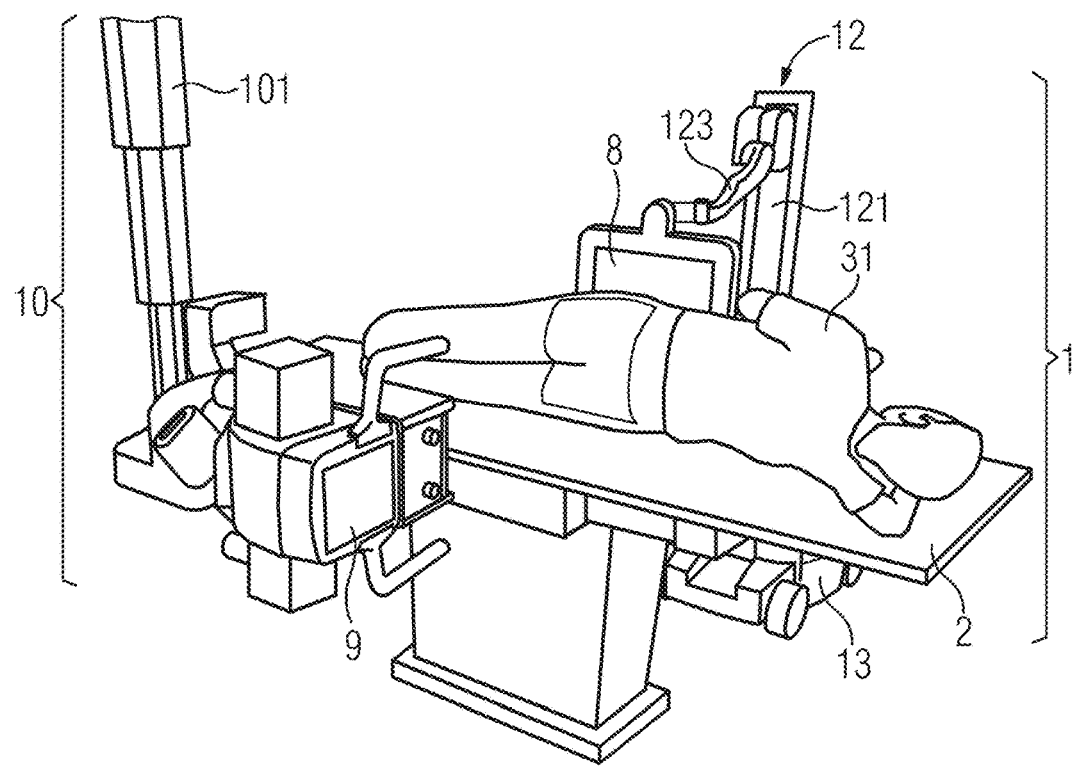
FIG. 8 shows a view of the example embodiment of the system in FIG. 7 from an alternative perspective.

FIG. 8 shows a view of the example embodiment of the system in FIG. 7 from an alternative perspective and with alternative positioning of the X-ray tube 9 and the X-ray detector 8. The X-ray tube 9 and the X-ray detector 8 are positioned in such a way that they can take an X-ray record of a body region of the patient 31. Positioning of the X-ray tube 9 can be performed on the basis of the coordination of the immobile platform 10 in the room. The immobile platform 10 can be coordinated in the environment analogously to the mobile platform 1 for this. Alternatively, the X-ray tube 9 can be positioned on the basis of the coordination of the immobile platform 10 by way of reference points, detected by an orientation sensor, on the patient couch 2 and/or with a patient detection sensor and the body region detection. The position or movement of the X-ray detector 8 can be adjusted to the position or movement of the X-ray tube 9. Matching can be performed analogously to the matching of medical devices between two mobile platforms 1.1, 1.2.

Alternatively, the mobile platform 1 can be coordinated in the environment and/or on the patient couch. In particular, the position or movement of the X-ray tube 9 can then be adjusted to the position or movement of the X-ray detector 8.

Freely movable/dynamic arrangements of the X-ray tube 9 in relation to the X-ray detector 8 can be adopted, therefore. In particular, radiological 2D and/or 3D image data can thus be acquired in varying poses and positions of the patient 31. Static and dynamic image recordings can be carried out.

Figure 9:
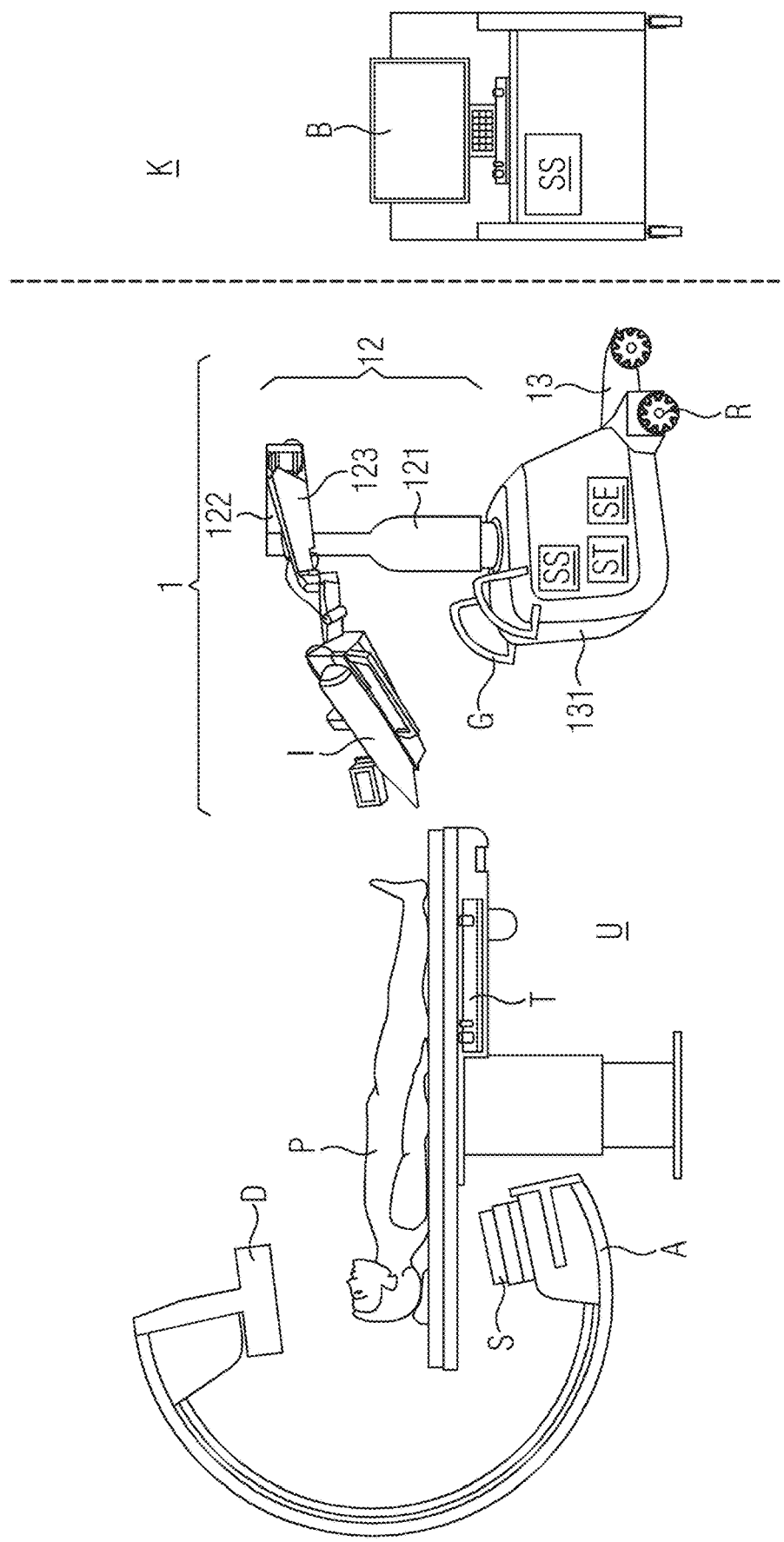
FIG. 9 shows a view of an example embodiment of an inventive mobile platform for (semi-) automatically performing a medical intervention.

FIG. 9 shows a view of an example embodiment of an inventive mobile platform for (semi-) automatic performance of a medical intervention.

The mobile platform 1 comprises a holding mechanism 12 and an omnidirectionally movable chassis 13.

The holding mechanism 12 comprises a housing 131. This has two hand grip elements G by which the mobile platform 1 can be pushed and moved in a manual or manually-assisted moving mode, in particular into a desired target position. The holding mechanism 12 comprises a lifting device 121 directly attached to the housing 131, a rotating device 122 attached to the lifting device 121 and a robotic actuator 123 attached to an end of the rotating device 122 remote from the lifting device. The robotic actuator 123 in turn comprises a large number of swivel joints and hinge joints. A first medical device in the form of an interventional platform I is arranged on the robotic actuator 123. The holding mechanism 12 is designed by way of its construction to completely cover, with the interventional platform I, an adjusting range, in particular directly on the patient P, and to bring the interventional platform I into any operating position. The floor-based omnidirectional chassis 13 and the holding mechanism 12 are oriented in the same spatial coordinate system.

In particular, movements of chassis 13 and holding mechanism 12 that are coordinated with each other can be carried out, therefore, in order to move the interventional platform I. Via omnidirectional chassis 13 having four omnidirectional Mecanum wheels R the mobile platform 1 can be moved in a medical environment, for example an examination room U, and, in particular, be brought close to a patient table T supporting the patient P. The traveling movement can occur manually, automatically, via remote control and/or (semi-) autonomously. The interventional platform I can be brought into a desired position relative to the patient P via the holding mechanism 12. The adjusting movement of the interventional platform I preferably occurs automatically and autonomously or via remote control.

The mobile platform also comprises a control unit ST, a sensor module SE and an interface unit SS.

The sensor unit SE is shown only as an example here. The sensor unit SE comprises at least one orientation sensor and at least one collision sensor. The sensor unit preferably comprises at least one collision sensor in the chassis 13, in the holding mechanism 12 and in the interventional platform I respectively. The sensors can be designed to generate sensor data, continuously or at intervals, for example by the second. The sensor data comprises, in particular, information about relative distances from second medical devices in the form of objects in the environment U, for example the patient table T, an angiography system A, the X-ray tube assembly S or detector D thereof, or relating to the patient P, and/or information relating to a position of the chassis 13 relative to a general reference point of the environment.

The control unit ST is designed to receive the sensor data via the interface unit SE and to use it for automatic generation of control signals for the chassis 13, the holding mechanism 12 and/or the interventional platform I. Control signals can relate, in particular to a movement speed, a stoppage of the movement, a direction of movement, a movement trajectory, a target position or the like for all or at least one of said units of the mobile platform 1. The control signals can be transmitted to the relevant units 12, 13, I via the interface unit SE.

The interface unit SS is used in this embodiment to also receive or send sensor data or control data/control signals to or from an operating unit B, which is arranged in a control room K spatially separate from the examination room U, and likewise comprises an interface unit SS. The operating unit B comprises an operating interface for a user, here comprising a large number of control elements such as keys, buttons, rotary knobs, joysticks or the like.

The user can input control commands relating to the movement or manipulation of the mobile platform 1, for the chassis 13, the holding mechanism 12, and/or, in particular, the interventional platform I via the operating interface. The user can control the movement of the mobile platform 1 and the progress of a medical intervention via the operating unit B. The operating unit B can furthermore be adapted to also receive control signals from a user for the angiography system A, in particular control signals for an adjusting movement of the angiography system A required by the intervention for image data acquisition and to send them via interface unit SE to the angiography system A.

This information can advantageously also be sent to the control unit ST of the mobile platform 1 to check whether the mobile platform 1 has to carry out an evasive movement in order not to disrupt X-ray imaging or to avoid a collision of interventional platform I or robotic actuator 123. Alternatively, information about a movement of the angiography system A can be acquired via the sensor module SE and be made available to the control unit ST for further processing.

Instead of an arithmetic unit provided in the mobile platform, the control unit ST can be designed as a central arithmetic unit and in particular carry out processing of sensor signals and/or generation of control signals for a plurality of mobile platforms of an inventive system.

The interface units SS preferably comprised input and output interfaces. The two interfaces can also be combined in one interface assembly, however. The interfaces SS can comprise, for example, hardware or software interfaces such as a PCI bus, USB or Firewire. Data is preferably exchanged via a network link or radio link. A network can be designed as a local area network (LAN), for example an intranet or a wide area network (WAN). The network link is inventively designed to be cable-free, for example as a wireless LAN (WLAN or WiFi). The network can comprise a combination of different network examples. Data can be transferred on the basis of a data retrieval or proactively. Data can be transferred bidirectionally or unidirectionally between two units or system components.

The control unit ST can be designed in the form of hardware or in the form of software. For example, the control unit ST is designed as what is known as an FPGA (acronym for "Field Programmable Gate Array") or comprises an arithmetic logic unit. The control unit ST can also be designed as an (independent) cloud-based computer, wherein data is exchanged with the sensor module or the operating unit B or units of the mobile platform 1 via a secure Internet connection.

In this embodiment of the invention, an interventional, robot-assisted platform for assisting, in particular, a cardiovascular and peripheral vascular intervention via guide catheters, guide wires, balloon implants or stent implants is advantageously designed to be mobile or portable and can be flexibly used for different procedures with different imaging systems, in particular angiography systems. Repositioning of the interventional platform without expert staff is also enabled by teleoperation. Since the interventional platform is mounted on the mobile platform 1, there is no additional load resting on the patient table. Collisions between angiography system and mobile platform can be avoided via sensor module and control unit. Steep angulations of the angiography system are possible by way of evasive maneuvers of the mobile platform. In an emergency the mobile platform along with interventional platform can be completely removed from patients in order to enable unimpeded access to the patient.

Although the invention has been illustrated and described in detail with reference to the preferred example embodiments it is not limited hereby. A person skilled in the art can derive other variations and combinations herefrom without departing from the fundamental idea of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A mobile platform, comprising
   a chassis;
   a sensor module including at least one orientation sensor configured to detect at least one reference point arranged in an environment of the mobile platform; and
   at least one holding mechanism configured to guide a first medical device, the at least one holding mechanism being configured to position the first medical device in at least one operating position within an adjusting range;
   wherein at least one of the chassis or the at least one holding mechanism are configured to adjust the at least one operating position of the first medical device attached to the at least one holding mechanism based on movement of a second medical device;
   wherein the second medical device is configured to be moved by a second mobile platform or an immobile platform; and
   wherein the second medical device is configured to communicate a position of the second medical device to the mobile platform.

2. The mobile platform of claim 1, wherein the first medical device is one of an X-ray detector, an X-ray tube, an ultrasound head, an endoscope, an interventional platform, a work light, a medical instrument or medical material.

3. The mobile platform of claim 2, wherein the at least one holding mechanism includes at least one of a lifting device, a rotating device, a robotic actuator and a manipulation device.

4. The mobile platform of claim 1, wherein the at least one holding mechanism includes at least one of a lifting device, a rotating device, a robotic actuator and a manipulation device.

5. The mobile platform of claim 4, wherein the sensor module includes at least one orientation sensor configured to detect at least one reference point arranged in an environment of the mobile platform.

6. The mobile platform of claim 4, wherein the sensor module includes at least one collision sensor configured to detect objects in an environment of the mobile platform.

7. The mobile platform of claim 4, wherein the sensor module includes at least one patient detection sensor.

8. The mobile platform of claim 1, wherein the sensor module includes at least one collision sensor configured to detect objects in an environment of the mobile platform.

9. The mobile platform of claim 1, wherein the sensor module includes at least one patient detection sensor.

10. The mobile platform of claim 1, wherein the at least one holding mechanism includes at least two holding mechanisms, and wherein the at least two holding mechanisms are configured to guide the first medical device and a third medical device and wherein the at least two holding mechanisms are configured to position the first medical device and the third medical device respectively, in the at least one operating position within an adjusting range.

11. The mobile platform of claim 10, further comprising: a battery module.

12. The mobile platform of claim 10, further comprising: an anti-tilt mechanism.

13. A The mobile platform of claim 1, further comprising: a battery module.

14. The mobile platform of claim 1, further comprising: an anti-tilt mechanism.

15. The mobile platform of claim 1, further comprising: a shelf space.

16. The mobile platform of claim 1, wherein the chassis is designed to be omnidirectional.

17. A system, comprising:
a plurality of mobile platforms, each of the plurality of mobile platforms including,
  a chassis,
  a sensor module including at least one orientation sensor configured to detect at least one reference point arranged in an environment of the mobile platform, and
  at least one holding mechanism configured to guide a first medical device, the at least one holding mechanism being configured to position the first medical device in at least one operating position within an adjusting range;
wherein at least one of the chassis or the at least one holding mechanism of a first one of the plurality of mobile platforms are configured to adjust the at least one operating position of the first medical device attached to the at least one holding mechanism based on movement of a second medical device;
wherein the second medical device is configured to be moved by a second one or the plurality of mobile platforms or an immobile platform; and
wherein the second medical device is configured to communicate a position of the second medical device to the first one of the plurality of mobile platform.

18. The system of claim 17, further comprising:
at least one immobile platform without a chassis, coordinated with the plurality of mobile platforms.

* * * * *